United States Patent
Peng et al.

(10) Patent No.: US 11,549,189 B1
(45) Date of Patent: Jan. 10, 2023

(54) ELECTROPLATING METHOD

(71) Applicant: Ming Chi University of Technology, New Taipei (TW)

(72) Inventors: Kun-Cheng Peng, New Taipei (TW); Wei-Chuan Shih, New Taipei (TW); Cheng-Rong He, New Taipei (TW); Ting-Han Chen, New Taipei (TW); Dong-Qing Su, New Taipei (TW); Jian-Rong Chen, New Taipei (TW)

(73) Assignee: Ming Chi University of Technology, New Taipei (TW)

( * ) Notice: Subject to any disclaimer, the term of this patent is extended or adjusted under 35 U.S.C. 154(b) by 0 days.

(21) Appl. No.: 17/686,433

(22) Filed: Mar. 4, 2022

(30) Foreign Application Priority Data

Jan. 21, 2022 (TW) ................................ 111102680

(51) Int. Cl.
| | |
|---|---|
| *C25D 3/02* | (2006.01) |
| *C25D 3/04* | (2006.01) |
| *C25D 3/10* | (2006.01) |
| *C25D 3/12* | (2006.01) |
| *C25D 3/22* | (2006.01) |
| *C25D 3/32* | (2006.01) |
| *C25D 3/38* | (2006.01) |
| *C25D 3/54* | (2006.01) |
| *C25D 17/00* | (2006.01) |
| *C12N 1/20* | (2006.01) |

(52) U.S. Cl.
CPC ................. *C25D 3/10* (2013.01); *C12N 1/20* (2013.01); *C25D 3/12* (2013.01); *C25D 3/22* (2013.01); *C25D 3/32* (2013.01); *C25D 3/38* (2013.01); *C25D 17/00* (2013.01)

(58) Field of Classification Search
CPC ... C25D 3/02; C25D 3/10; C25D 3/12; C25D 3/22; C25D 3/32; C25D 3/38; C25D 3/04; C25D 3/54
USPC ....... 205/261, 269, 271, 283, 291, 300, 305, 205/290, 296, 302, 311
See application file for complete search history.

(56) References Cited

U.S. PATENT DOCUMENTS

| | | | | |
|---|---|---|---|---|
| 6,528,424 B1 * | 3/2003 | Lopatin | ..................... | C25D 5/18 257/E21.175 |
| 2003/0060873 A1 * | 3/2003 | Gertner | ...................... | A61P 7/02 623/1.42 |

FOREIGN PATENT DOCUMENTS

CN 109537031 A * 3/2019 ............. C25D 17/00

* cited by examiner

*Primary Examiner* — Edna Wong

(57) ABSTRACT

The present disclosure provides an electroplating method, comprising providing an electroplating solution, wherein the electroplating solution includes an effective microorganisms aqueous solution and metal chloride; disposing a workpiece, wherein at least a part of the workpiece is in contact with the electroplating solution; and performing an electroplating process to electroplate metal of the metal chloride onto the workpiece.

7 Claims, 7 Drawing Sheets

ELECTROPLATING METHOD

CROSS REFERENCE TO RELATED DISCLOSURE

This application claims the priority benefit of Taiwan Patent Application Number 111102680, filed on Jan. 21, 2022, the full disclosure of which is incorporated herein by reference.

BACKGROUND

Technical Field

The present disclosure is related to electroplating, and in particular, an electroplating method.

Related Art

The electroplating process is one of the common surface treatment techniques employed in modern industry. The method is to place the product to be electroplated in an electroplating tank with an electroplating solution and then form a coating on the surface of the product by the principle of electrolysis. As a result, the coating may prevent the product from oxidation (for example, rust) and provide a visually pleasing effect to the product. However, contaminants from the electroplating process, such as used electroplating solutions, surface impurities, and metal deposits, may seriously pollute water sources and greatly harm the surrounding environment.

In addition, the electroplating solutions may be categorized into two types: cyanide and non-cyanide. Wherein, cyanide-based electroplating solutions are favored by traditional industries and become the mainstream due to good stability thereof. However, cyanide-based electroplating solutions are themselves highly toxic. The use of highly toxic electroplating solutions not only damages the environment but also causes serious harm to the body of the operator. Therefore, with the increasing awareness of environmental protection, how to provide an electroplating solution that is safe, environmentally friendly, and easy to store has become an urgent issue to be solved.

SUMMARY

The embodiments of the present disclosure disclose an electroplating method, in order to solve the problem that the electroplating solutions used for the present electroplating method are not environmentally friendly, unsafe, and difficult to store.

In order to solve the above technical problems, the present disclosure is implemented as follows.

The present disclosure provides an electroplating method comprising: providing an electroplating solution, wherein the electroplating solution includes effective microorganism aqueous solution and metal chloride; disposing a workpiece, wherein at least a part of the workpiece is in contact with the electroplating solution; performing an electroplating process to electroplate metal of the metal chloride onto the workpiece.

In some embodiments of the present disclosure, the microorganism aqueous solution includes 0.1 vol % to 1.0 vol % of nitrogen, 0.1 vol % to 1.0 vol % of potassium dioxide, and 1 vol % to 20 vol % of organic substances, and the remaining part are effective microorganisms and water.

In some embodiments of the present disclosure, a working temperature of the electroplating process is within 20° C. to 60° C.

In some embodiments of the present disclosure, a working current of the electroplating process is within 0.04 A to 1.5 A.

In some embodiments of the present disclosure, a working voltage of the electroplating process is within 0.02 V to 7.5 V.

In some embodiments of the present disclosure, the metal chloride is at least one of the copper chloride, nickel chloride, cobalt chloride, chromium chloride, and tin chloride.

In some embodiments of the present disclosure, the volume molar concentration of the metal chloride is within 0.3 M to 0.6 M.

In some embodiments of the present disclosure, the effective microorganism may include one or more than one of photosynthetic bacteria series, *Lactobacillus* series, yeast series, fungus series, and actinobacteria series.

In the embodiments of the present disclosure, the electrochemical reaction may be stably performed by using the effective microorganism as the conductive substance in the electroplating solution, thereby realizing the effect of electroplating. In addition, the effective microorganism is a material that is safe, non-toxic, and easy to store. The effective microorganism is not harmful to the environment, either before or after use. Therefore, the present disclosure is disclosed an electroplating method effectively solving the problem that the electroplating solution in the prior art is harmful to the environment.

BRIEF DESCRIPTION OF THE DRAWINGS

The figures described herein are used to provide a further understanding of the present disclosure and constitute a part of the present disclosure. The exemplary embodiments and descriptions of the present disclosure are used to illustrate the present disclosure and do not limit the present disclosure, in which.

DETAILED DESCRIPTION OF THE EMBODIMENTS

In order to make the objectives, technical solutions, and advantages of the present disclosure clearer, the technical solutions of the present disclosure will be described clearly and completely in conjunction with specific embodiments and the figures of the present disclosure. Obviously, the described embodiments are only a part of the embodiments of the present disclosure, rather than all the embodiments. Based on the embodiments in the present disclosure, all other embodiments obtained by a person of ordinary skill in the art without creative work fall within the protection scope of the present disclosure.

The following description is of the best-contemplated mode of carrying out the present disclosure. This description is made for the purpose of illustrating the general principles of the present disclosure and should not be taken in a limiting sense. The scope of the present disclosure is best determined by reference to the appended claims.

Moreover, the terms "include", "contain", and any variation thereof are intended to cover a non-exclusive inclusion. Therefore, a process, method, object, or device that comprises a series of elements not only includes these elements, but also comprises other elements not specified expressly, or may include inherent elements of the process, method, object, or device. If no more limitations are made, an element limited by "include a/an . . . " does not exclude other same elements existing in the process, the method, the article, or the device which comprises the element.

Figure 1:
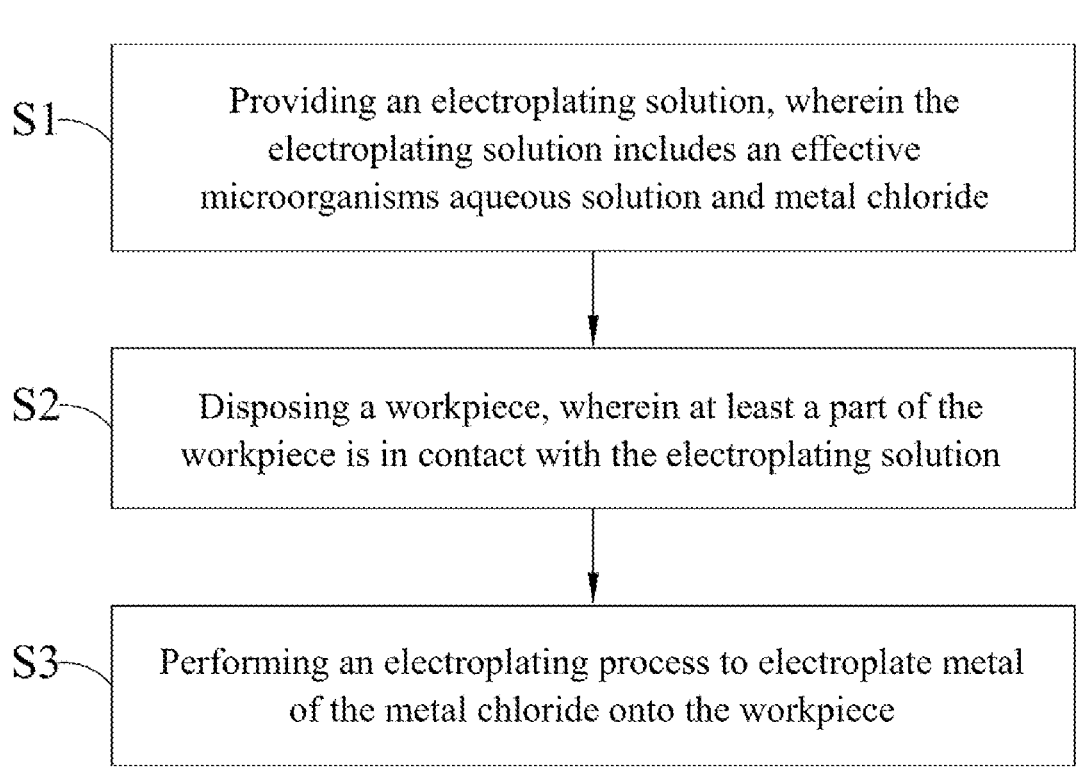
FIG. 1 is the flowchart of the electroplating method according to an embodiment of the present disclosure.

FIG. 1 is the flowchart of the electroplating method according to an embodiment of the present disclosure. As shown in the figure, the electroplating method includes:

Step S1: Providing an electroplating solution, wherein the electroplating solution includes an effective microorganisms aqueous solution and metal chloride. It should be noted that the common additives well known by a person having ordinary skill in the art may be added into the electroplating solution, and the addition of the additives is low (for example, total concentration thereof is lower than 10 wt % or 10 vol %). Therefore, the main solvent (or the main reactive substance) of the electroplating solution in the present disclosure still is the effective microorganism aqueous solution, and the concentration of the effective microorganism aqueous solution is more than 50 vol % in the entire electroplating solution.

In some embodiments, the effective microorganism aqueous solution may consist of the effective microorganism and pure water only, but the present disclosure is not limited thereto. In other embodiments, the effective microorganism aqueous solution may further contain nitrogen and/or carbon source. For example, the effective microorganism aqueous solution may be formed by mixing of dried effective microorganism (or powder) and water, or the effective microorganism aqueous solution may consist of the effective microorganism and cultivating environment (contains water, carbon, and nitrogen source) thereof. It should be noted that various additives (for example, nutritional agents) well known by a person having ordinary skill in the art may also be added to the effective microorganisms aqueous solution of the present disclosure to maintain the survival rate of the effective microorganisms. That is, the present disclosure is not limited to the compose mentioned above.

In some embodiments, in addition to the effective microorganism and water, the effective microorganism aqueous solution may also contain 0.1 vol % to 1.0 vol % of nitrogen (refer to total nitrogen or pure nitrogen), 0.1 vol % to 1.0 vol % of potassium dioxide, and 1 vol % to 20 vol % of organic substances. For example, the concentration of nitrogen in the effective microorganism aqueous solution may be 0.1 vol %, 0.2 vol %, 0.3 vol %, 0.4 vol %, 0.5 vol %, 0.6 vol %, 0.7 vol %, 0.8 vol %, 0.9 vol %, 1.0 vol %, or any range of the combinations of the numerals mentioned above. The concentration of potassium dioxide in the effective microorganism aqueous solution may be 0.1 vol %, 0.2 vol %, 0.3 vol %, 0.4 vol %, 0.5 vol %, 0.6 vol %, 0.7 vol %, 0.8 vol %, 0.9 vol %, 1.0 vol %, or any range of the combinations of the numerals mentioned above. The concentration of organic substances in the effective microorganism aqueous solution may be 1 vol %, 5 vol %, 10 vol %, 15 vol %, 20 vol %, or any range of the combinations of the numerals mentioned above. Preferably, the effective microorganism aqueous solution contains 0.6 vol % of nitrogen, 0.8 vol % of potassium dioxide, and 9.3 vol % of organic substance.

In some embodiments, the effective microorganisms may include one or more than one of photosynthetic bacteria series, *Lactobacillus* series, yeast series, fungus series, and actinobacteria series, but the present disclosure is not limited thereto. For example, *Lactobacillus* may be *Lactobacillus acidophilus*, *Bifidobacterium* species, and *Lactobacillus casei*. In some embodiments, the effective microorganisms may consist of 80 different microorganism species, and the microorganism species may include but not be limited to the microorganisms mentioned above.

In some embodiments, the effective microorganism aqueous solution may directly use the 5-14 liquid miscellaneous organic fertilizer with the registration number of the fertilizer system (quality) No. 0495006 (Agriculture and Food Agency Council of Agriculture, the Executive Yuan of Taiwan). More specifically, the microorganisms in the liquid miscellaneous organic fertilizer may include nitrogen fixing bacteria series, nitrifying bacteria series, phosphoric acid releasing series, photosynthetic bacteria series, *Lactobacillus* series, yeast series, actinobacteria series, and growth factors producing bacteria series. In addition to the microorganisms mentioned above, the liquid miscellaneous organic fertilizer may further contain molasses, urea, egg, canavanine powder, and water.

The function of metal chloride in the electroplating solution is mainly to provide the source of metallic ions. Therefore, the specific type of metal chloride used in the electroplating solution depends on the metal to be electroplated. For example, when the metal to be electroplated is copper, the metal chloride is copper chloride. In some embodiments, the metal chloride may be at least one of copper chloride, nickel chloride, cobalt chloride, chromium chloride, zinc chloride, and tin chloride. As mentioned above, when the numeral of metal to be electroplated is more than two, more than two metal chloride may be added to the electroplating solution. Therefore, two metals may be plated onto the workpiece at the same time.

In some embodiments, a volume molar concentration of metal chloride in electroplating solution may be within 0.3 M to 0.6 M. For example, the volume molar concentration of metal chloride may be 0.3 M, 0.35 M, 0.40 M, 0.45 M, 0.50 M, 0.55 M, 0.60 M, or any range of the combinations of the numerals mentioned above. The molar concentration of the metal chloride may be related to deposition time. In the case of the coating's thickness being fixed, decreasing the volume molar concentration of metal chloride in the electroplating solution may cause an increase in deposition time but a raise in the coating's surface quality. On the other hand, increasing the volume molar concentration of metal chloride in the electroplating solution may cause a decrease in deposition time but a reduction in the coating's surface quality.

Step S2: Disposing the workpiece, and at least a part of the workpiece is in contact with the electroplating solution. The workpiece is electrically conductive or at least partially conductive, and the workpiece is electrically connected to a cathode of a power supply. In some embodiments, the workpiece may be metal or other material coated with a metallic layer on the surface. For example, the workpiece may include copper or alloys thereof.

Step S3: Performing an electroplating process to electroplate metal of the metal chloride onto the workpiece. In the present disclosure, the electroplating process may be: connecting the workpiece to the negative electrode of the power supply and making the positive electrode of the power supply be in contact with the electroplating solution; then, turning on the power supply so that the power supply, the electroplating solution, and the workpiece form a conductive loop. When the conductive loop exists, the metal ions of the electroplating solution receive electrons and adhere to the workpiece, thereby realizing the electroplating effect. It should be noted that the descriptions mentioned above are only examples, and the present disclosure is not limited thereto. In practical applications, a person having ordinary skill in the art may use various conventional electroplating equipment, electroplating steps, configuration details, etc. to perform electroplating processes similar to those described above.

In some embodiments, a working temperature of the electroplating process may be within 20° C. to 60° C. For example, the working temperature of the electroplating process may be 20° C., 25° C., 30° C., 35° C., 40° C., 45° C., 50° C., 55° C., 60° C., or any range of the combinations of the numerals mentioned above. For electroplating solutions mainly composed of effective microorganisms, a working temperature that is too high (for example, greater than 60° C.) will lead to a too fast electrochemical reaction, resulting in poor coating quality. Conversely, a working temperature that is too low (for example, less than 20° C.) will lead to a too slow electrochemical reaction, even ineffective to deposit metal on the workpiece. Therefore, the working temperature of the electroplating process is preferably within the range mentioned above. Furthermore, since the electroplating solution of the present disclosure may perform the electroplating process at room temperature (for example, between 20° C. and 30° C.), the present disclosure may also greatly reduce energy consumption (for example, energy consumed by heating), thereby reducing carbon emissions.

In some embodiments, a working current of the electroplating process may be within 0.04 A to 1.5 A. For example, the working current may be 0.04 A, 0.1 A, 0.2 A, 0.3 A, 0.4 A, 0.5 A, 0.6 A, 0.7 A, 0.8 A, 0.9 A, 1.0 A, 1.1 A, 1.2 A, 1.3 A, 1.4 A, 1.5 A, or any range of the combinations of the numerals mentioned above. Similar to the working temperature, a working current that is too high (for example, greater than 1.5 A) will lead to a too fast electrochemical reaction, resulting in poor coating quality. Conversely, a working current that is too low (for example, less than 0.04 A) will lead to a too slow electrochemical reaction, even ineffective to deposit metal on the workpiece. Therefore, the working current of the electroplating process is preferably within the range mentioned above.

In some embodiments, a working voltage of the electroplating process may be within the range of 0.02 V to 7.5 V. For example, the working current may be 0.02 V, 0.5 V, 1.0 V, 1.5 V, 2.0 V, 2.5 V, 3.0 V, 3.5 V, 4.0 V, 4.5 V, 5.0 V, 5.5 V, 6.0 V, 6.5 V, 7.0 V, 7.5 V, or any range of the combinations of the numerals mentioned above. Similar to the working temperature, a working voltage that is too high (for example, greater than 7.5V) will lead to a too fast electrochemical reaction, resulting in poor coating quality. Conversely, a working voltage that is too low (for example, less than 0.02V) will lead to a too slow electrochemical reaction, even ineffective to deposit metal on the workpiece. Therefore, the working voltage of the electroplating process is preferably within the range mentioned above.

Table 1 lists the different process parameters for producing different coatings, respectively. In order to validate the effect of the present disclosure, the examples shown in Table 1 will be employed for demonstration.

TABLE 1

|  | 1$^{st}$ embodiment | 2$^{nd}$ embodiment | 3$^{rd}$ embodiment | 4$^{th}$ embodiment | 5$^{th}$ embodiment |
| --- | --- | --- | --- | --- | --- |
| Metal chloride | Chromium chloride | Tin chloride | Copper chloride | Zinc chloride | Cobalt chloride |
| Working current | 0.04 A | 0.15 A | 0.02 A | 0.02 A | 0.06 A |
| Working voltage | 7.5 V | 0.1 V | 4.4 V | 9.4 V | 0.4 V |
| Plating time | 2 hr | 2 hr | 2 hr | 2 hr | 2 hr |
| Coating | Chromium | Tin | Copper | Zinc | Cobalt |

Figure 2:
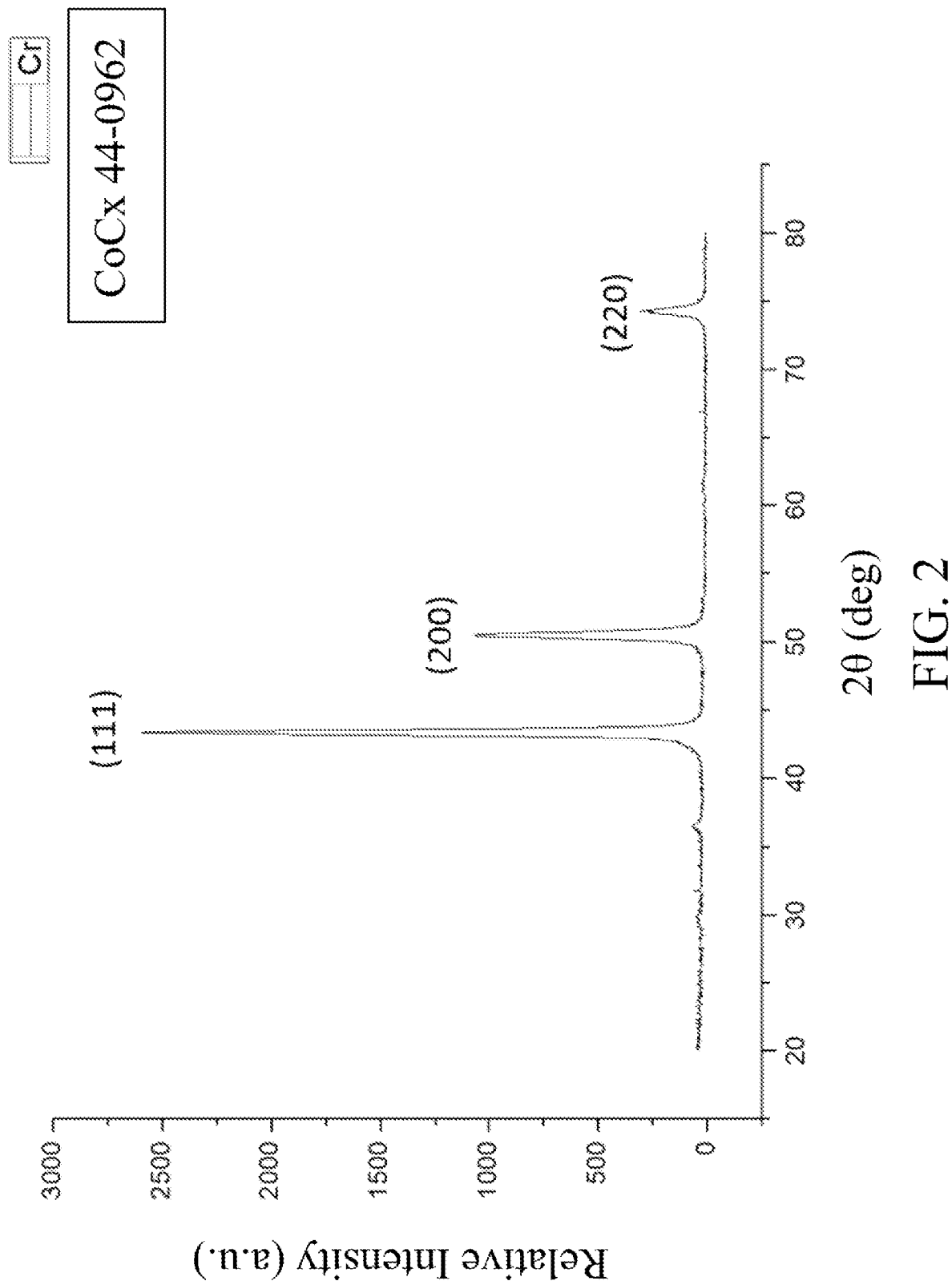
FIG. 2 to FIG. 6 respectively are the measured X-ray diffraction spectra of the coatings performed by the electroplating method according to the first embodiment of the present disclosure.
Figure 3:
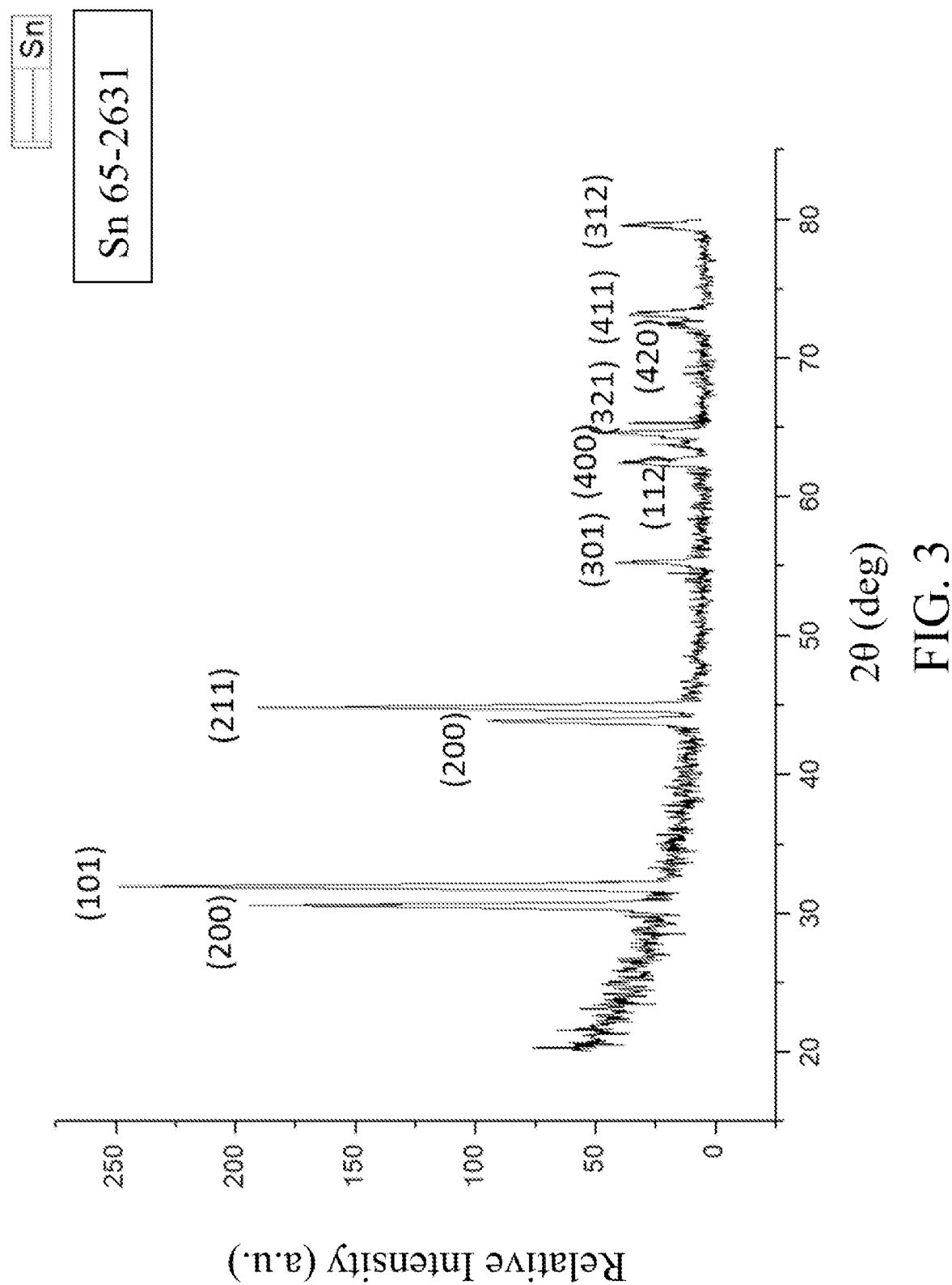
Figure 4:
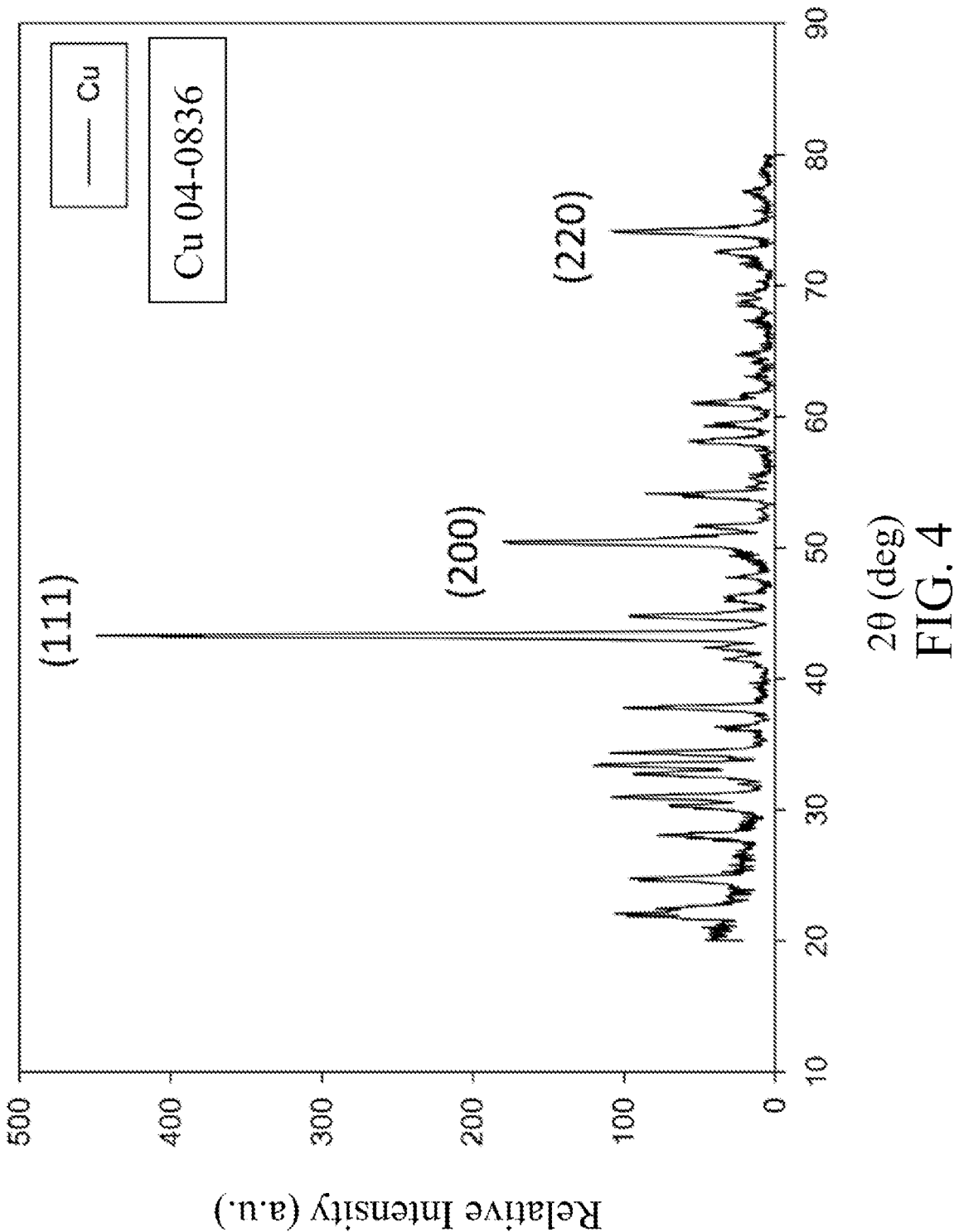
Figure 5:
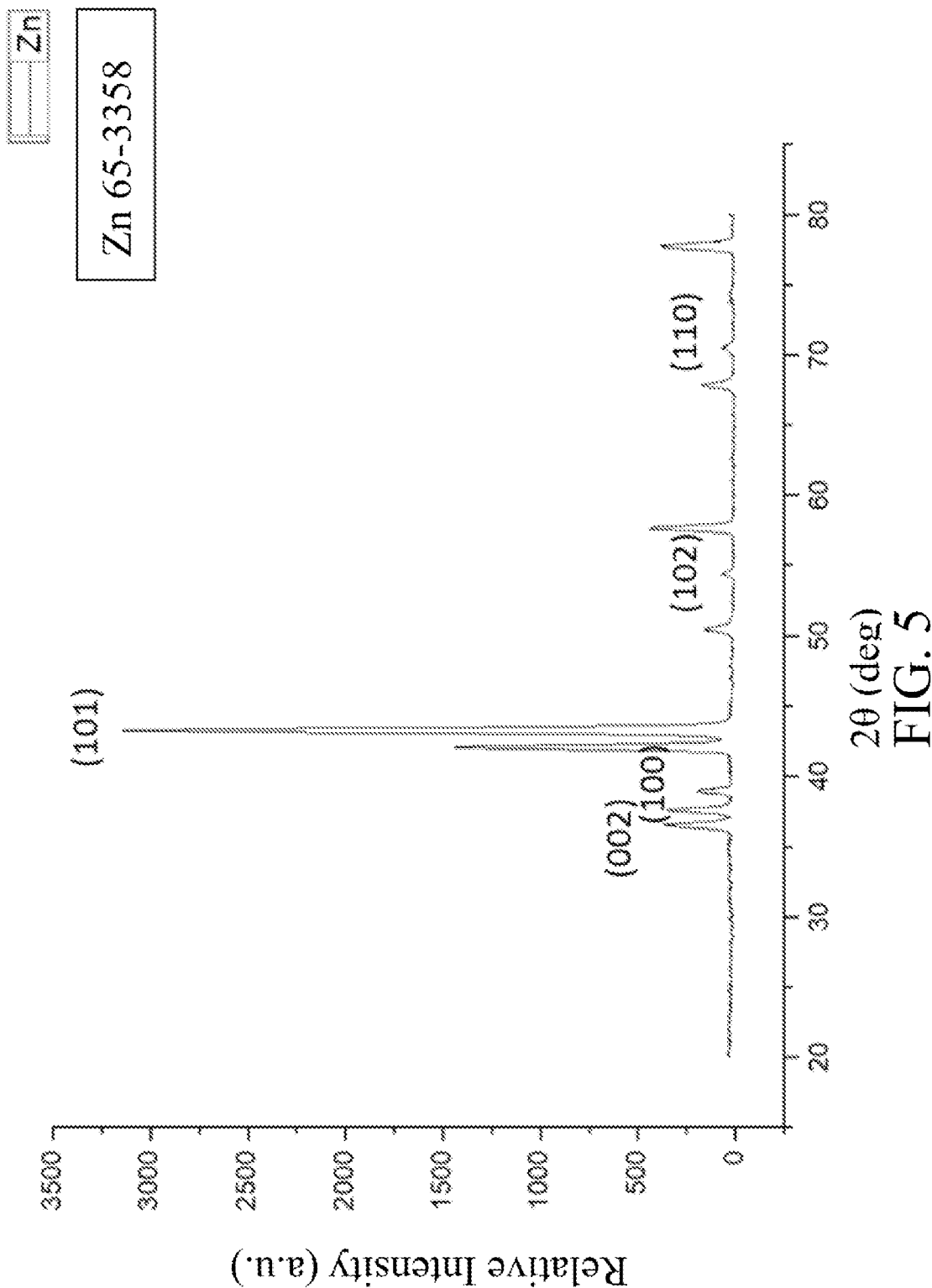
Figure 6:
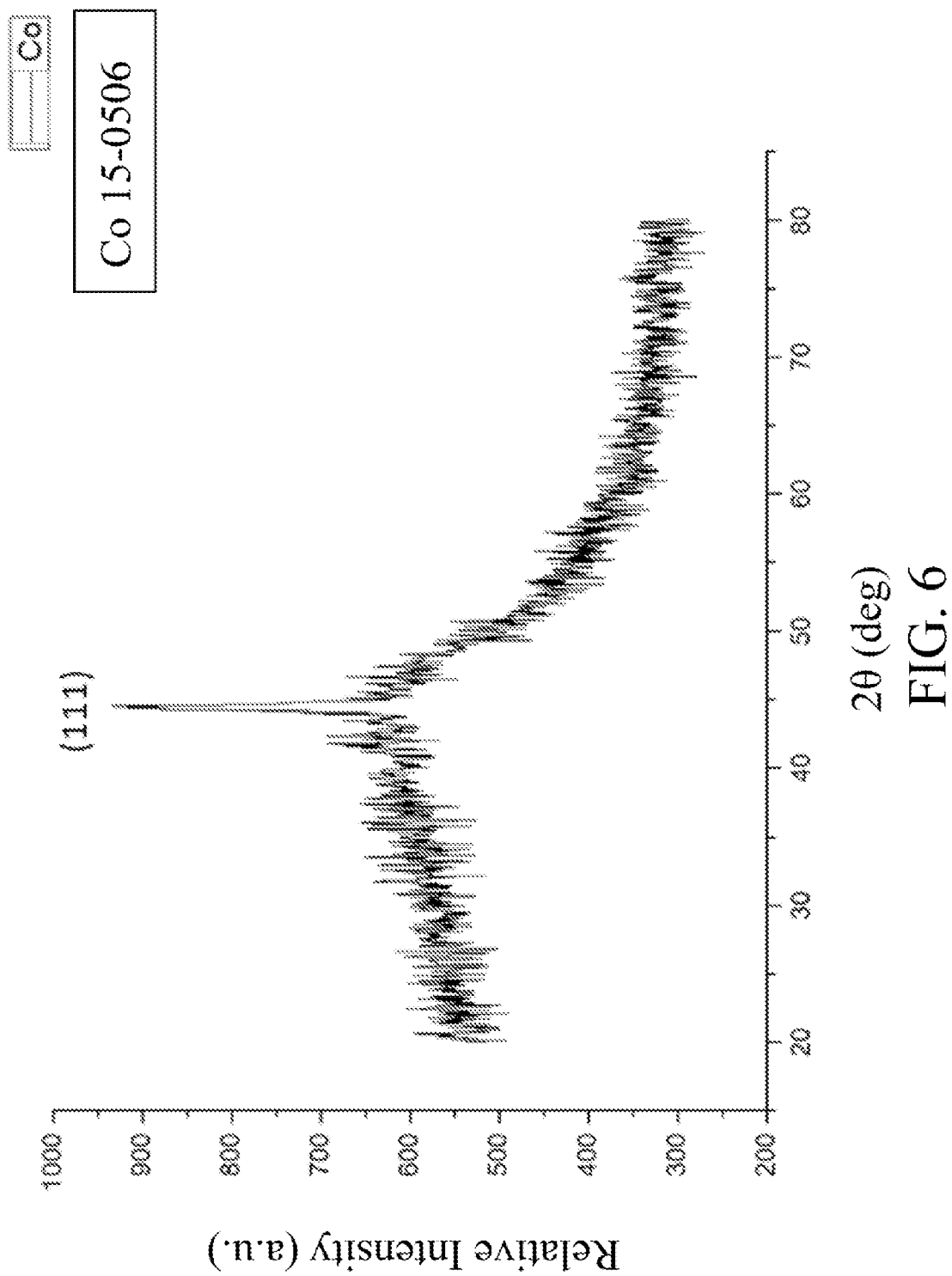

FIG. 2 to FIG. 6 respectively are the measured X-ray diffraction spectra of the coatings performed from by the electroplating method according to an embodiments of the present disclosure. More specifically, FIG. 2 is the X-ray diffraction spectrum of a chromium coating, which shows the diffraction peaks of Cr at (111), (200), and (220). FIG. 3 is the X-ray diffraction spectrum of a tin coating, which shows the diffraction peaks of Sn at (101), (112), (200), (211), (301), (312), (321), (400), (411), and (420). FIG. 4 is the X-ray diffraction spectrum of a copper coating, which shows the diffraction peaks of Cu at (111), (200), and (220). FIG. 5 is the X-ray diffraction spectrum of a chromium coating, which shows the diffraction peaks of Zn at (002), (100), (101), (102), and (110). FIG. 6 is the X-ray diffraction spectrum of a cobalt coating, which shows the diffraction peaks of Co at (111). From the results in Table 1 and the X-ray diffraction results presented in FIG. 2 to FIG. 6, the electroplating solution in the present disclosure may be used in the electroplating process. However, the electroplating method of the present disclosure is not limited by the metal material mentioned above.

Figure 7:
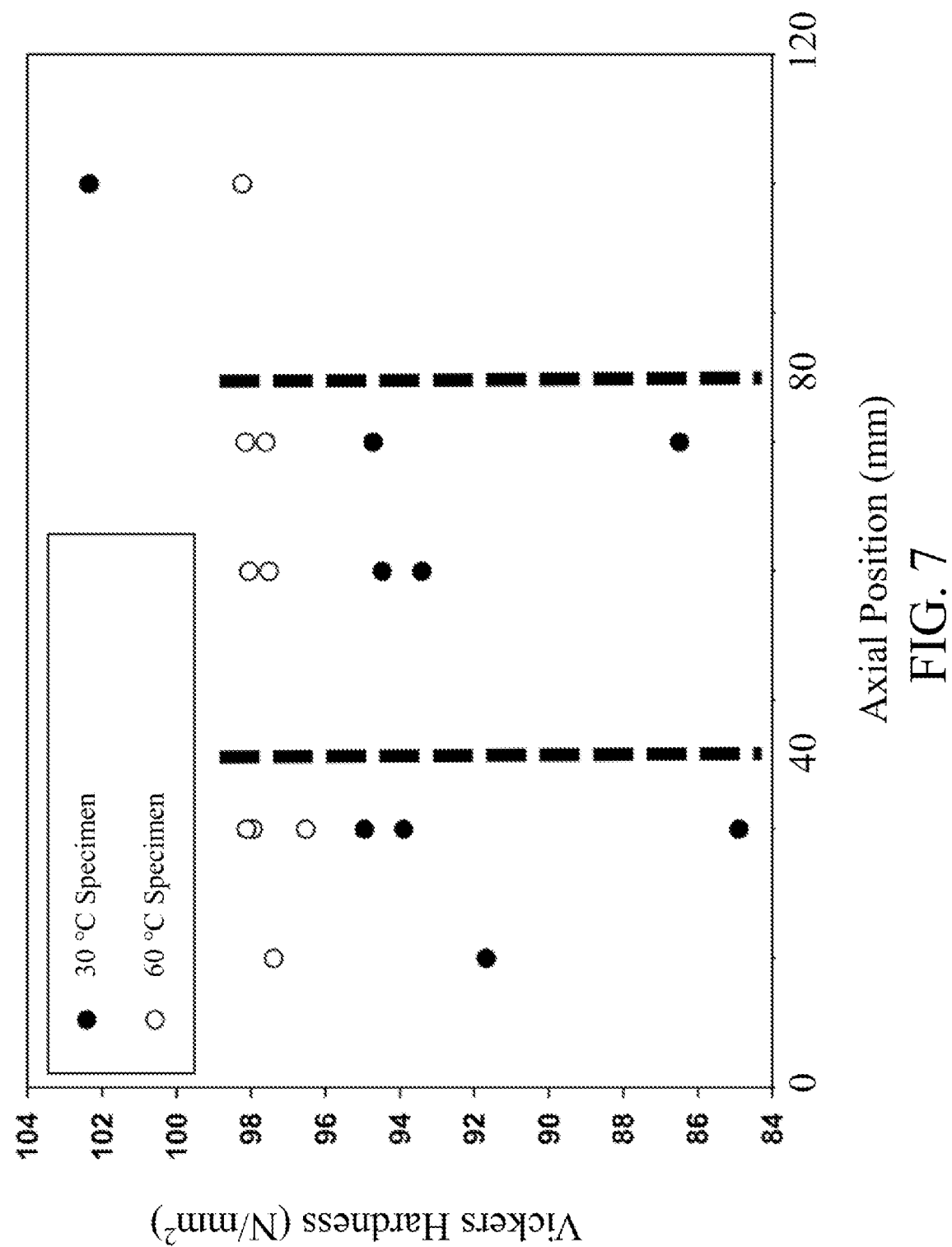
FIG. 7 is the hardness test result of the coatings performed by the electroplating method according to an embodiment of the present disclosure.

FIG. 7 is the hardness test result of the coatings performed by the electroplating method according to an embodiment of the present disclosure. More specifically, FIG. 7 presents the hardness of coatings prepared from electroplating processes with different working temperatures, respectively. As shown in the figure, for the same Vickers hardness indentation, coatings prepared from lower working temperatures have lower strengths, while coatings prepared from higher working temperatures have higher strengths. For metallic coating, the hardness denotes the resistance of the material to plastic deformation caused by lattice distortion (defects of dislocation, interstitial atoms, vacancy, etc.). In other words, the working temperature is not only affected the deposition rate but also the internal stress. Therefore, after considering the test result and the description mentioned above, the conclusion hereinafter may be obtained. When the temperature is higher than 60° C., the coating is not uniform or even peeling due to excessive hardness (which may be regarded as large internal stress). Conversely, when the temperature is lower than 20° C., the coating may not be attached due to too small hardness (which may be regarded as insufficient adhesion).

On the other hand, FIG. 7 further shows that the coatings have different harnesses at different locations. Specifically, the left area of FIG. 7 represents the end of the workpiece away from the power source (that is, the end away from the electroplating solution level), the right area of FIG. 7 represents the end of the workpiece close to the power source (that is, the end close to the electroplating solution level), and the middle area in FIG. 7 represents the area between the two ends of the workpiece. From the test results, the farther away from the power supply end has greater internal stress, which may be caused by the greater concentration of effective microorganisms in the electroplating solution therein. Therefore, in some cases, the concentration of the electroplating solution may be made more consistent by changing the electroplating tank, so that the coating layer on the whole workpiece has a similar hardness.

In summary, in the embodiments of the present disclosure, the electrochemical reaction may be stably performed by using the effective microorganism as the conductive substance in the electroplating solution, thereby realizing the effect of electroplating. In addition, the effective microorganism is a material that is safe, non-toxic, and easy to store. The effective microorganism is not harmful to the environment, either before or after use. Therefore, the present disclosure is disclosed an electroplating method effectively solving the problem that the electroplating solution in the prior art is harmful to the environment.

Although the present disclosure has been explained in relation to its preferred embodiment, it does not intend to limit the present disclosure. It will be apparent to those skilled in the art having regard to this present disclosure that other modifications of the exemplary embodiments beyond those embodiments specifically described here may be made without departing from the spirit of the invention. Accordingly, such modifications are considered within the scope of the invention as limited solely by the appended claims.

What is claimed is:

1. An electroplating method, comprising:
   providing an electroplating solution, wherein the electroplating solution includes an effective microorganisms aqueous solution and a metal chloride, and the effective microorganisms aqueous solution comprises 0.1 vol % to 1.0 vol % of nitrogen, 0.1 vol % to 1.0 vol % of potassium dioxide, and 1 vol % to 20 vol % of organic substance, and the remaining part are effective microorganisms and water;
   disposing a workpiece, wherein at least a part of the workpiece is in contact with the electroplating solution; and
   performing an electroplating process to electroplate metal of the metal chloride onto the workpiece.

2. The electroplating method of claim 1, wherein a working temperature of the electroplating process is within 20° C. to 60° C.

3. The electroplating method of claim 1, wherein a working current of the electroplating process is within 0.04 A to 1.5 A.

4. The electroplating method of claim 1, wherein a working voltage of the electroplating process is within 0.02 V to 7.5 V.

5. The electroplating method of claim 1, wherein the metal chloride is at least one of copper chloride, nickel chloride, cobalt chloride, chromium chloride, zinc chloride, and tin chloride.

6. The electroplating method of claim 1, wherein a volume molar concentration of the metal chloride is within 0.3 M to 0.6 M.

7. The electroplating method of claim 1, wherein the effective microorganisms comprise one or more than one of photosynthetic bacteria series, *Lactobacillus* series, yeast series, fungus series, and actinobacteria series.

* * * * *